(12) United States Patent
Weaver et al.

(10) Patent No.: US 8,266,956 B2
(45) Date of Patent: *Sep. 18, 2012

(54) PROCESS FOR DEMONSTRATING TISSUE PRODUCT BREAK-THROUGH

(75) Inventors: Gregg Thomas Weaver, Liberty Township, OH (US); Michael Scott Prodoehl, West Chester, OH (US); LaTisha Evette Salaam, Leesburg, GA (US); Joseph Jay Bullock, Lebanon, OH (US); Elizabeth Ann Kreider, Hamilton, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 374 days.

This patent is subject to a terminal disclaimer.

(21) Appl. No.: 12/481,671

(22) Filed: Jun. 10, 2009

(65) Prior Publication Data

US 2010/0313648 A1 Dec. 16, 2010

(51) Int. Cl.
*G01L 5/04* (2006.01)
*G01N 1/00* (2006.01)
*G01N 17/00* (2006.01)

(52) U.S. Cl. .......... 73/159; 530/836; 73/863; 73/865.6; 73/865.8; D20/31; D20/32

(58) Field of Classification Search .......... 73/159; 162/198, 263
See application file for complete search history.

(56) References Cited

U.S. PATENT DOCUMENTS

| 5,013,403 A * | 5/1991 | Chase ............... 162/49 |
| 6,430,989 B1 | 8/2002 | Van Dyke et al. |
| 2005/0258199 A1 | 11/2005 | Honer et al. |
| 2007/0048709 A1 | 3/2007 | Ales, III et al. |

FOREIGN PATENT DOCUMENTS

WO WO 2005/031068 A1 4/2005

OTHER PUBLICATIONS

Ross, B.B., et al., "Physical Dynamics of the Cough Mechanism", *Cough Dynamics*, vol. 8, Nov. 1955, pp. 264-268.

* cited by examiner

*Primary Examiner* — Lisa Caputo
*Assistant Examiner* — Roger Hernandez-Prewitt
(74) *Attorney, Agent, or Firm* — Peter D. Meyer

(57) ABSTRACT

A method for demonstrating the comparative break-though strengths of at least two tissue products is disclosed. The steps include: a) providing a break-through test apparatus b) providing the tissue products; c) observing a first condition of each tissue product; d) disposing a first of the tissue products between a lower platen and an upper platen in a face-to-face-to-face relationship between coextensive apertures disposed within the lower and upper platen; e) providing a simulated mucous composition; f) directing a first portion of the simulated mucous composition toward the first tissue product; g) observing a second condition of the first tissue product; h) disposing a second tissue product between the coextensive apertures; i) directing a second portion of the simulated mucous composition toward the second tissue product; j) observing a second condition of the second tissue product; and, k) comparing the second condition of the first tissue product and the second condition of the second tissue product.

20 Claims, 5 Drawing Sheets

PROCESS FOR DEMONSTRATING TISSUE PRODUCT BREAK-THROUGH

FIELD OF THE INVENTION

The present invention relates to a process for qualitatively demonstrating the break-through of sanitary tissue products such as bath and facial tissues. More particularly, the present invention relates to a qualitative method for demonstrating the break-through differences between two or more bath or facial tissue products.

BACKGROUND OF THE INVENTION

Consumers continue to demand significantly improved properties in their bath and facial tissue products. As a result, manufacturers are constantly attempting to improve these critical products to provide the improved properties that make a bath or facial tissue that is more desired by consumers. However, these same manufacturers can be provided with difficulty in trying to communicate the particular superior technical aspects of the bath or facial tissue product in a manner that is meaningful to a consumer.

The consumer is typically flooded with a wealth of data, technical characteristics, marketing, and puffery that relate to the bath and facial tissue products. However, it can be difficult for a consumer to understand the technical nuances of each of the data presented by the manufacturer.

The manufacturer desires to present this meaningful and purposeful communications to the consumer in a meaningful, clear, and/or visual manner that compares one bath or facial tissue product to others. However, to date no one has been able to provide such a meaningful, clear, and/or visual comparative manner to consumers. This is particularly true about the break-through strength of bath and facial tissue products.

Users of facial tissues can be presented with a conundrum. Many brands of facial tissue are marketed with slogans such as, "It feels good to feel" indicating that the tissue may be soft. However, a soft tissue that 'feels good' may be provided with insufficient strength to prevent that same consumer from becoming soiled with body exudates that are supposed to be captured by the facial tissue. In typical use, a facial tissue is used by a consumer to blow their nose. However, as may happen all too often, the expectorated mucous, water, and other otorhinolaryngological discharges egressing from the nasolabial area onto a facial tissue cause the facial tissue to catastrophically fail. This leaves the expelled mucous, water, and other otorhinolaryngological discharges upon the consumer's hands. Yuck!

Thus, by providing a clear and fair standard for publicly and qualitatively demonstrating the break-through strength of a facial tissue or bath tissue, the manufacturer can communicate this critical information to a consumer. Accordingly, there is a need for an apparatus and method to qualitatively demonstrate to a consumer the break-through property differences between two or more bath or facial tissue products.

SUMMARY OF THE INVENTION

One embodiment of the present disclosure is directed toward a method of demonstrating the comparative break-though strengths of at least two tissue products. The method comprises the steps of: a) providing a break-through test apparatus having a lower platen and an upper platen disposed in a face-to-face relationship; b) providing the at least two tissue products; c) observing a first condition of each of the at least two tissue products; d) disposing a first of the at least two tissue products between the lower platen and the upper platen in a face-to-face-to-face relationship; e) disposing at least a portion of the first tissue product between an aperture disposed within the lower platen and a coextensive aperture disposed within the upper platen; f) providing a simulated mucous composition; g) directing a first portion of the simulated mucous composition toward the first tissue product disposed within the coextensive apertures; h) after step g), observing a second condition of the first tissue product; i) disposing a second of the at least two tissue products between the lower platen and the upper platen in a face-to-face-to-face relationship and a portion of the second tissue product between the coextensive apertures; j) directing a second portion of the simulated mucous composition toward the second tissue product disposed within the coextensive apertures; k) after step j), observing a second condition of the second tissue product; and, l) comparing the second condition of the first tissue product and the second condition of the second tissue product.

Another embodiment of the present disclosure provides a method of demonstrating the comparative break-though strengths of at least two tissue products. The method comprises the steps of: a) providing a first break-through test apparatus having a lower platen and an upper platen disposed in a face-to-face relationship; b) providing a second break-through test apparatus having a lower platen and an upper platen disposed in a face-to-face relationship; c) providing the at least two tissue products; d) observing a first condition of the at least two tissue products; e) disposing a first of the at least two tissue products between the lower platen and said upper platen of the first break-through test apparatus in a face-to-face-to-face relationship; f) disposing a portion of the first tissue product between an aperture disposed within the lower platen and a coextensive aperture disposed within the upper platen of the first break-through test apparatus; g) disposing a second of the at least two tissue products between the lower platen and the upper platen of the second break-through test apparatus in a face-to-face-to-face relationship; h) disposing a portion of the second tissue product between an aperture disposed within the lower platen and a coextensive aperture disposed within the upper platen of the second break-through test apparatus; i) providing a simulated mucous composition; j) directing a first portion of the simulated mucous composition toward the first tissue product disposed within the coextensive apertures of the first break-through test apparatus and a second portion of the simulated mucous composition toward the second tissue product disposed within the coextensive apertures of the second break-through test apparatus; k) observing a second condition of each of the first and second tissue products; and, l) comparing the second condition of the first tissue product and the second condition of said second tissue product.

DETAILED DESCRIPTION OF THE INVENTION

Figure 1:
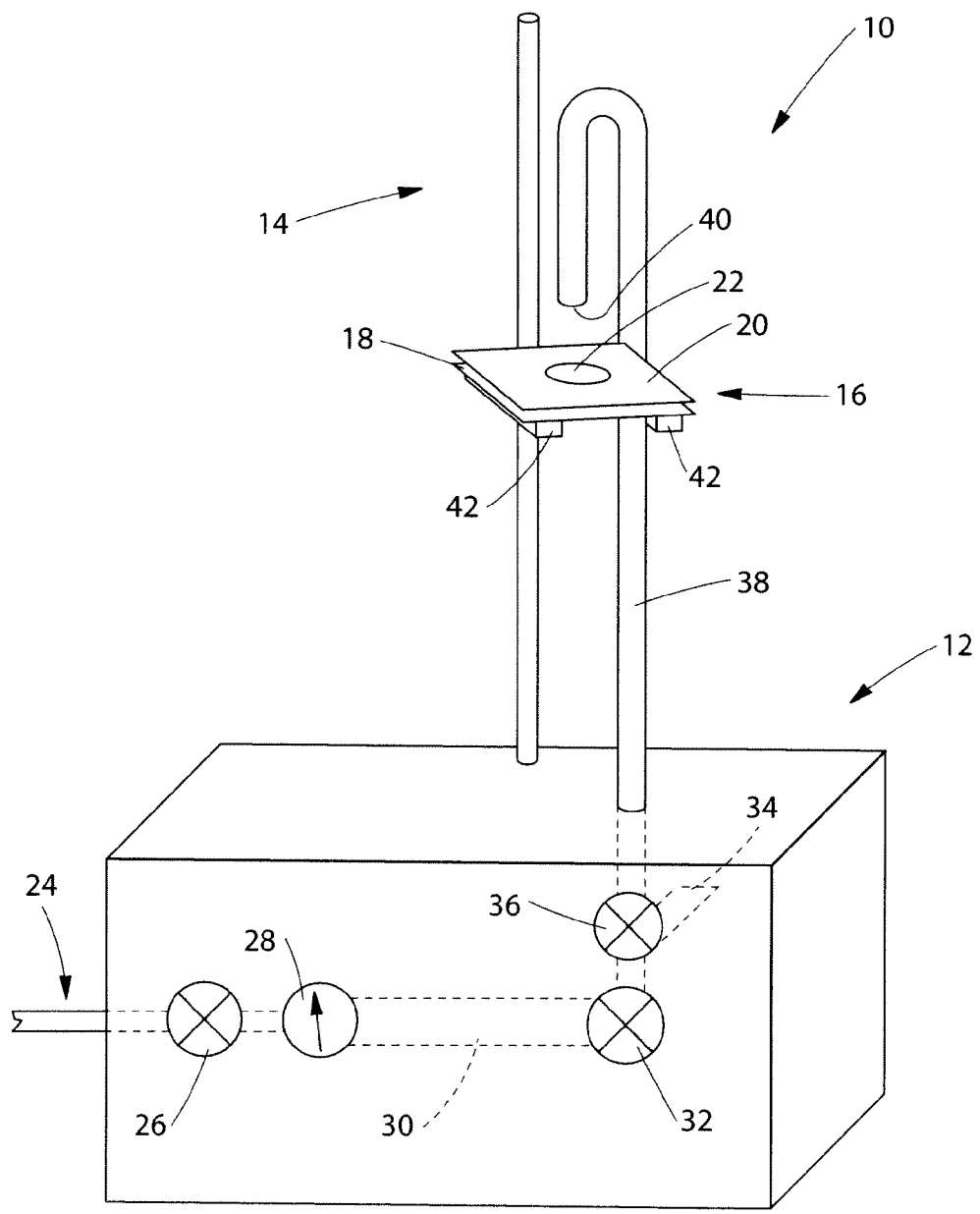
FIG. 1 is a perspective view of an exemplary tissue break-through test apparatus in accordance with the present disclosure.

The instant invention can be neatly parsed into three easily recognizable portions. These are: 1) an exemplary apparatus for demonstrating the break-though of a tissue product; 2) an exemplary process for demonstrating the break-though of a tissue product; and 3) an exemplary comparative method for demonstrating the break-though of a tissue product to a consumer. The description of each section of the apparatus and process is described forthwith.

Non-limiting examples of processes for making fibrous structures suitable for use in conjunction with the apparatus and method of the present disclosure include known wet-laid fibrous structure making processes, air-laid fibrous structure making processes, melt-blowing fibrous structure making processes, co-forming fibrous structure making processes, and spun-bond fibrous structure making processes. Such processes typically include steps of preparing a fiber composition, oftentimes referred to as a fiber slurry in wet-laid processes, either wet or dry, and then depositing a plurality of fibers onto a forming wire or belt such that an embryonic fibrous structure is formed, drying and/or bonding the fibers together such that a fibrous structure is formed, and/or further processing the fibrous structure such that a finished fibrous structure is formed. The fibrous structure may be a through-air-dried fibrous structure and/or conventionally dried fibrous structure. The fibrous structure may be creped or un-creped. The fibrous structure may exhibit differential density regions or may be substantially uniform in density. The fibrous structure may be pattern densified, conventionally felt-presses and/or high-bulk, un-compacted. The fibrous structures may be homogenous or multilayered in construction.

After and/or concurrently with the forming of the fibrous structure, the fibrous structure may be subjected to physical transformation operations such as embossing, calendering, selfing, printing, folding, softening, ring-rolling, applying additives, such as latex, lotion and softening agents, combining with one or more other plies of fibrous structures, and the like to produce a finished fibrous structure that forms and/or is incorporated into a sanitary tissue product.

A "tissue product" or a "bath and facial tissue" as used herein means a wiping implement for post-urinary and/or post-bowel movement cleaning (toilet tissue), for otorhinolaryngological discharges (facial tissue) and/or multi-functional absorbent and cleaning uses (absorbent towels such as paper towels and/or wipes). The bath and facial tissue products of the present invention may comprise one or more fibrous structures and/or finished fibrous structures.

The bath and facial tissue products suitable for use in conjunction with the apparatus and method of the present disclosure may exhibit a basis weight between about $10 \text{ g/m}^2$ to about $120 \text{ g/m}^2$ and/or from about $15 \text{ g/m}^2$ to about $110 \text{ g/m}^2$ and/or from about $20 \text{ g/m}^2$ to about $100 \text{ g/m}^2$ and/or from about 30 to $90 \text{ g/m}^2$ and/or from about $29 \text{ g/m}^2$ to about $51 \text{ g/m}^2$ The bath and facial tissue products suitable for use in conjunction with the apparatus and method of the present disclosure may exhibit a wet burst value of greater than about 40 g and/or ranging from between about 40 g and about 150 g and/or ranging from between about 60 g to about 130 g.

The bath and facial tissue products suitable for use in conjunction with the apparatus and method of the present disclosure may exhibit a density of less than about $0.60 \text{ g/cm}^3$ and/or less than about $0.30 \text{ g/cm}^3$ and/or less than about $0.20 \text{ g/cm}^3$ and/or less than about $0.10 \text{ g/cm}^3$ and/or less than about $0.07 \text{ g/cm}^3$ and/or less than about $0.05 \text{ g/cm}^3$ and/or from about $0.01 \text{ g/cm}^3$ to about $0.20 \text{ g/cm}^3$ and/or from about $0.02 \text{ g/cm}^3$ to about $0.10 \text{ g/cm}^3$ and/or from about $0.10 \text{ g/cm}^3$ to about $0.20 \text{ g/cm}^3$ and/or from about $0.05 \text{ g/cm}^3$ to about $0.25 \text{ g/cm}^3$.

The bath and facial tissue products suitable for use in conjunction with the apparatus and method of the present disclosure may be in any suitable form, such as in a roll, in individual sheets, in connected, but perforated sheets, in a folded format, in an unfolded format, or as a plurality of individual folded sheets in an inter-folded format. Additionally, bath and facial tissue products suitable for use in conjunction with the apparatus and method of the present disclosure may comprises additives such as softening agents, temporary wet strength agents, permanent wet strength agents, bulk softening agents, lotions, silicones, and other types of additives suitable for inclusion in and/or on sanitary tissue products.

"Ply" or "plies" as used herein means an individual finished fibrous structure. A plurality of plies may be optionally disposed in a substantially contiguous, face-to-face relationship with other plies, forming a multiple ply (or "multi-ply") product suitable for use in conjunction with the apparatus and method of the present disclosure. It is also contemplated that a single-ply bath and facial tissue products suitable for use in conjunction with the apparatus and method of the present disclosure can effectively form two "plies" or multiple for purposes of the present disclosure by being folded upon itself.

Apparatus

As shown in FIG. 1, the break-through test apparatus 10 of the present disclosure can be used to simulate, replicate, and/or otherwise provide for the imitation of a typical human sneeze. As one of skill in the art will readily recognize, a sneeze is the emission of air or breath suddenly, forcibly, and audibly through the nose and mouth by an involuntary, spasmodic action. The break-through test apparatus 10 comprises generally a box 12 and test stand 14. The test stand 14 preferably comprises a sample holder 16 having a lower platen 18 and an upper platen 20. Both the lower platen 18 and upper platen 20 are provided with apertures therein. By way of example, upper platen 20 is provided with an upper platen aperture 22, as shown. Lower platen 18 is similarly provided with a lower platen aperture (not shown) similar to the upper platen aperture 22 disposed within upper platen 20. In a preferred embodiment of the present invention the upper platen aperture 22 and the lower platen aperture are coextensive, meaning their peripheries are similar in shape and size and over-lie one another.

The box 12 supporting break-through test apparatus 10 is preferably fluidly connected to a source of compressed air 24. The plumbing associated with the break-through test apparatus 10 and disposed within box 12 can preferably provide for the storage and maintenance (either short- or long-term) of the compressed air emanating from the source of compressed air 24. By way of non-limiting example, a charging valve 26 and pressure regulator 28 can allow for compressed air to enter an air accumulator 30 for storage, pressurization therein, and eventual emanation therefrom.

A synthetic (or synthesized) mucous sample mimicking an otorhinolaryngological discharge (the formulation is described infra) is placed within dosing inlet 34 and is combined with the compressed air stored within air accumulator 30 upon release of the compressed air from air accumulator 30 through exhaust valve 32. It should be realized by one of skill in the art that any natural or synthetic otorhinolaryngological discharge may be used with the apparatus and method of the present disclosure. The combined synthetic mucous and air mixture that is positioned within dose addition assembly 36 is then vented through tubing 38 and expelled through opening (or nozzle) 40. The expelled synthetic mucous/air mixture is then disposed upon a tissue product sample to be qualitatively tested by the break-through test apparatus 10.

The tissue product sample is preferably positioned intermediate, and in a face-to-face relationship between, lower platen 18 and upper platen 20. At least a portion of the tissue product sample is exposed through upper platen aperture 22 and an aperture (not shown) positioned within lower platen 18. Lower platen 18 and upper platen 20 may be supported by any means known to those of skill in the art suitable for supporting such devices such as a sample holder 16. In any regard, it is preferred that sample holder 16, lower platen 18, and upper platen 20, and an exemplary tissue product sample suitable for testing and positioned therebetween be fixably supported so that during testing sample holder 16, lower platen 18, and upper platen 20 are subject to minimal, and preferably no, movement. Such support can be provided by horizontal support members 42 extending outwardly from test stand 14.

Figure 2:
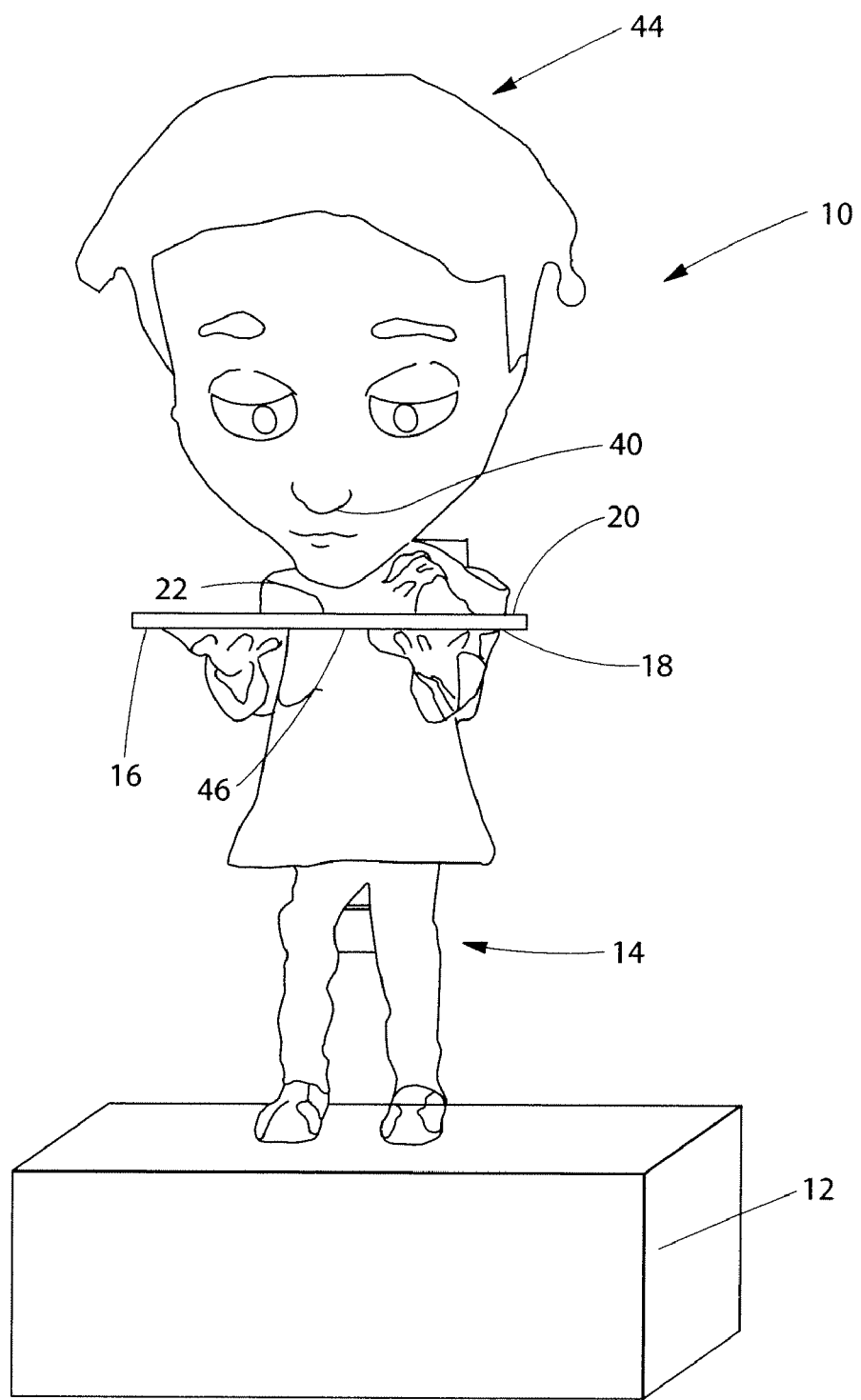
FIG. 2 is a perspective view of the exemplary break-through test apparatus of FIG. 1 wherein a mannequin in the form of a well known commercial character encapsulates the break-through test apparatus.

Turning now to FIG. 2, the break-through test apparatus 10, comprising box 12, test stand 14, and sample holder 16, can be contained within, and camouflaged by, the use of a mannequin 44. By way of non-limiting example, mannequin 44 can be any character or caricature suitable for use in demonstrating the qualitative break-through strength of a facial tissue sample by the use of break-through test apparatus 10. Exemplary, but non-limiting caricatures suitable for use as mannequin 44 can include characters associated with a particular brand of product, cartoons, movie stars, politicians, other famous people, and the like. In any regard, it is preferable to conceal the inner workings of break-through test apparatus 10 as this was found to provide additional credence to the results obtained through the use of the break-through test apparatus 10.

By use of a mannequin 44, it is preferred that the mannequin 44 be positioned so as to coordinate the expectoration of the simulated mucous and air mixture (i.e., the simulated otorhinolaryngological discharge) with the nasolabial area of the caricature 44. It was found that this arrangement provided a more realistic example of the break-through test apparatus 10. In this regard, opening 40 of test stand 14 can be positioned within the nasolabial area of the mannequin 44. Thus, when the simulated mucous/air mixture is expectorated from opening 40 disposed within mannequin 44 onto a portion of the tissue product sample disposed between with upper platen 20 and lower platen 18 and within upper platen aperture 22 and lower platen aperture 46 of sample holder 16 respectively, a more realistic representation of a human sneeze is provided. In other words, it is preferred that the simulated mucous/air mixture exit the nasolabial area of mannequin 44 through opening 40 and be displaced through upper platen aperture 22 disposed within upper platen 20 onto a tissue product positioned between lower platen 18 and upper platen 20.

Process

Figure 3:
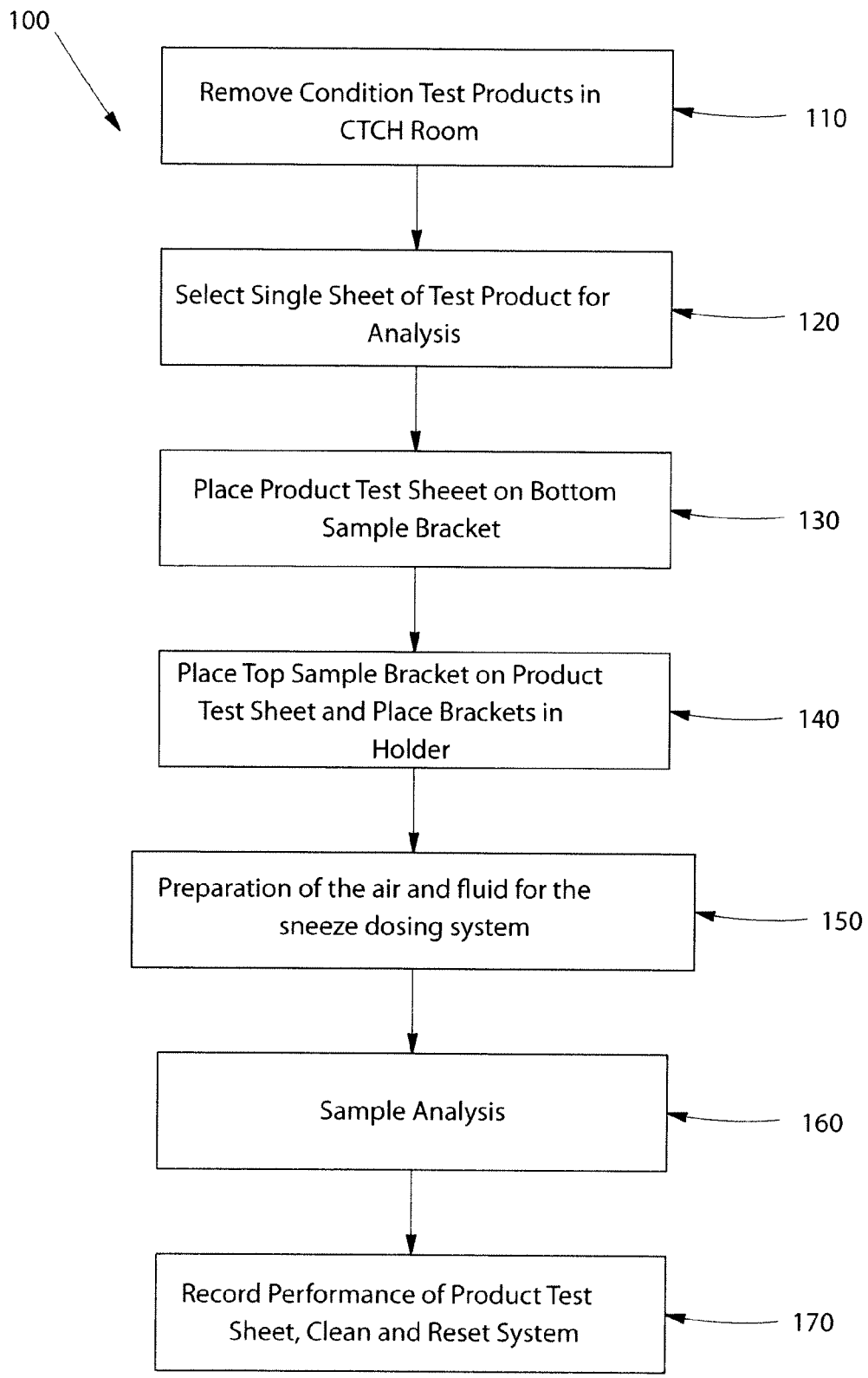
FIG. 3 is an exemplary flow diagram detailing exemplary steps for use of the break-through test apparatus of FIG. 1.

FIG. 3 depicts a flow diagram illustration of several exemplary steps suitable for use with the break-through test apparatus 10 found helpful in qualitatively evaluating the break-through strength of an exemplary tissue product. The overall method 100 is composed of a series of sequential steps selected to mimic and/or simulate how a consumer or consumers would utilize tissue products such as bath and facial tissues under real life conditions. It should be realized that the overall method 100 may be done in a comparative manner so that the consumer can evaluate how different tissue products within an array of branded products or how tissue products associated with different brands will perform under similar use conditions. The steps and conditions may be selected based on actual consumer in-use conditions as reported in the scientific literature or can be based upon known clinical data.

The first step 110 of method 100 of the exemplary disclosed process is to simply select a tissue product or at least two tissue products for a sequential or a side-by-side comparison of the tissue products. It should be easily realized by one of skill in the art that the apparatus and process of the present disclosure should not be limited merely to the testing of tissue products. Rather, the apparatus and process of the present disclosure could be used to test and/or demonstrate a wide variety of consumer products such as food wraps, foils, film, woven substrates, non-woven substrates, air-laid substrates, and the like. In any regard the tissue samples to be tested by the apparatus and processes of the present disclosure are preferably fibrous structures and/or bath and facial tissue product samples and/or hand sheets that have been conditioned in an air conditioned room at a temperature of 73° F.±4° F. (23° C.±2.2° C.) and a relative humidity of about 50%±10% for 2 hours prior to any testing. It is preferred, but not required, that the exemplary disclosed process be conducted in an air conditioned room. In any regard, the tissue samples to be tested should be subjected to the above-described conditioning for at least about 2 hours prior to testing. Approximately 60 sheets of each tissue sample product to be used for testing are removed from their primary packaging and stored in the open at the constant temperature and humidity as described above.

The second step 120 of method 100 provides for the removal of a single tissue product sample sheet or tissue product from the stack of tissue product samples to be used for testing. It is preferred that the first two sheets and the last two sheets of each such stack of tissue product samples (or other consumer products to be tested) not be used.

The third step 130 of method 100 provides for the placement of a single sheet of tissue product sample in a coextensive and face-to-face relationship upon lower platen 18 of sample holder 16. Lower platen 18 is provided with a lower platen aperture 46 disposed within (and preferably centrally located within) lower platen 18. Thus, the tissue sample to be tested should be positioned upon the lower platen 18 of sample holder 16 in a face-to-face relationship that effectively covers and conceals the lower platen aperture 46. In one example, lower platen 18 is provided as an 8-inch×8-inch× ¼-inch (20.3 cm×20.3 cm×0.64 cm) thick sheet of Plexiglas®. Lower platen aperture 46 can be provided as a 2.5-inch (6.35 cm) hole cut within the center portion of the Plexiglas® sheet forming lower platen 18. In a preferred embodiment, the tissue product sample to be tested is smoothed out and centered over the lower platen aperture 46 within the central portion of lower platen 18 without overstretching or distorting the tissue product sample.

The fourth step 140 of method 100 provides for the placement of upper platen 20 having upper platen aperture 22 centrally disposed therein in a face-to-face relationship, and coextensive, with the second surface of the tissue product sample disposed upon lower platen 18. In a preferred embodiment, upper platen 18 is provided as an 8-inch×8-inch×⅜-inch (20.3 cm×20.3 cm×0.95 cm) thick sheet of Plexiglas®. The upper platen aperture 22 is preferably provided as a 2.5-inch (6.35 cm) hole positioned centrally within upper platen 20. An upper platen 20 formed from such an 8-inch×

8-inch×⅜-inch (20.3 cm×20.3 cm×0.95 cm) thick sheet of Plexiglas® material was found to weigh approximately 140 g.

Upper platen 20 is aligned with lower platen 18 so that lower platen aperture 46 and upper platen aperture 22 are aligned and coextensive with the same portion of the tissue sample to be tested. It should be realized that the tissue sample to be tested and disposed between lower platen 18 and upper platen 20 is positioned to be smooth and flat and held in place only by the weight of upper platen 20 disposed in the face-to-face-to-face relationship with lower platen 18. It was surprisingly found that this configuration can allow for the tissue product sample to be tested to deform slightly when the simulated mucous and air mixture is directed toward the upper platen aperture 22 from opening 40 of test stand 14. In other words, lower platen 18 and upper platen 20 are not clamped together in any fashion and no additional weight is placed upon upper platen 20 during testing of a tissue product sample. As one of skill in the art will readily appreciate, this configuration simulates the deformation of a tissue product when an air mass with entrained mucous, water, and other otorhinolaryngological discharges is directed toward the tissue product sample under pressure just as the tissue product sample would likely deform within a consumer's hands when utilized as would be intended by one of skill in the art. It is preferred that the opening 40 of test stand 14 be disposed proximate to, and above, upper platen aperture 22 of upper platen 20 in order to effectively simulate a real life sneeze. In this regard, it was found useful that upper platen aperture 22 be disposed approximately 1-inch±0.15-inch (2.54 cm±0.38 cm) from opening 40 of test stand 14. Thus, as the air mass with entrained mucous, water, and other otorhinolaryngological discharges is directed toward the tissue product sample disposed within the region circumscribed by upper platen aperture 22 under pressure, the air mass is disposed upon the tissue product sample disposed within the region circumscribed by upper platen aperture 22 and not upon any regions of upper platen 22 outside the region circumscribed by upper platen aperture 22.

The fifth step 150 of method 100 provides for preparation of the break-through test apparatus 10 for use. In operation, the exhaust valve 32 is closed and charging valve 26 of box 12 is opened. Compressed air is then disposed within air accumulator 30 until the air pressure within air accumulator 30 is approximately 40 lb/in$^2$ (2.72 atm) as measured by pressure regulator 28. It should be realized by one of skill in the art that any amount of air pressure can be provided within air accumulator 30. When the desired pressure is reached, charging valve 26 is closed. It was found for purposes of the testing of facial tissue that the air accumulator 30 have a total volume of about 180 ml. It was found that this 180 ml volume at approximately 40 lbs/in$^2$ (2.72 atm) was equivalent to about 2.5 liters of air at atmospheric pressure. It is believed that this volume of air is consistent with the volume of air expelled by the average human during a normal sneeze.

Next, approximately 0.5 ml±0.05 ml of simulated mucous is added to the box 12 through dosing inlet 34. The simulated mucous is then translated from dosing inlet 34 to dose addition assembly 36 for eventual combination and mixing with the compressed air stored within air accumulator 30.

A simulated mucous used as the test fluid has been developed to have a sheer thinning viscosity (i.e., is thixotropic behavior) similar to that of a typical nasal discharge. The simulated mucous is prepared according to the following directions. The materials required include 2.70 g carboxymethyl cellulose (CMC), 0.75 g methyl paraben (MP), and 500 ml distilled water. The equipment required includes a 1,000 ml beaker, hot plate, thermometer, 40-ounce commercial blender, and a stopwatch.

500 ml of distilled water is heated to 55° C.±2° C. 400 ml of this heated water is poured into a blender with the blender cover put in place. Approximately ⅓ of 0.75 gm methyl paraben (MP) is added. The mixture is blended at a medium blender speed with the remaining MP slowly added. Next, 2.70 g carboxymethyl cellulose (CMC) is added to the MP/water mixture. After addition of the CMC to the MP/water mixture, the remaining 100 ml of heated distilled water is added. This mixture is blended for an additional 2 minutes. At this point the CMC should be dissolved in the water and have a viscosity of 180±28 centipoise. If the CMC is not dissolved, additional blending is done until the CMC is dissolved. If the viscosity of the simulated mucous is below the desired target viscosity, additional CMC is added incrementally and dissolved until the desired target viscosity is achieved. If the viscosity of the simulated mucus is above the desired target viscosity, the solution is diluted with heated distilled water incrementally and mixed until the target viscosity is achieved. The resulting simulated mucous is stored in a covered plastic container.

It is preferred that the simulated mucous solution equilibrate prior to testing of any samples. The simulated mucous should be conditioned for at least 4 hours at 23° C.±1° C. and 50% plus or minus 2% relative humidity prior to testing. It was found that the simulated mucous provided herein has a viscosity consistent with the viscosity of mucous typically expelled by a human during a normal sneeze.

Returning again to FIG. 3, with further reference to FIG. 1, the dose addition assembly 36 provides for the simulated mucous to be added and/or injected into the flow path of the compressed air between the exhaust valve 32 and the opening 40 of test stand 14 while preventing the compressed air from flowing out the dosing inlet 34 when the exhaust valve 32 is opened and compressed air is forced through the tubing disposed between dose addition assembly 36 and opening 40. The dose addition assembly 36 provides for the simulated mucous to accumulate in a zone within the tubing 38 approximately 20-inches±2-inches (50.8 cm±5.1 cm) from opening 40. It was found that this can be accomplished by providing a loop in the tubing 38 that creates a low spot in the tubing approximately 20-inches (50.8 cm) from the opening 40. Alternatively, the simulated mucous can be positioned at the exit of exhaust valve 32 as long as exhaust valve 32 is positioned approximately 20-inches (50.8 cm) from opening 40 through tubing 38. It was surprisingly found by the use of a series of high speed videography examination of the fluid pattern of the simulated mucous expunged from opening 40 through the analysis of droplet size distribution and droplet velocity that 20-inches (50.8 cm) provides for an optimal mixing of simulated mucous and air and remarkably simulates a normal human sneeze. In other words, a 20-inch (50.8 cm) travel within tubing 38 for the simulated mucous, when combined with approximately 2.5 liters of air forced through the tubing 38 and exiting at opening 40 delivered a fluid pattern consistent with that achieved and observed from a typical human sneeze. While not desiring to be bound by theory, it is believed that the length of tubing 38 provided at approximately 20-inches (50.8 cm) allows sufficient interaction and impingement of any larger simulated mucous droplets in the tubing 38 walls as they are forced along the inside of the tubing 38 by the compressed air to break up any overly large droplets of the simulated mucous into a mixture of smaller droplets. This is surprisingly similar to what happens within the air passageway when a human sneezes.

Alternatively, it was found that dose addition assembly 36 and dosing inlet 34 can be provided optionally if the test stand 14 is designed so that any simulated mucous can be disposed into the system via the opening 40 and be allowed to drain back down the tubing 38 at lengths of at least about 20-inches±2-inches (50.8 cm±5.1 cm).

The sixth step 160 of method 100 provides for sample analysis. Exhaust valve 32 of box 12 is opened thereby allowing the compressed air to exit the system via the tubing 38 and opening 40. The simulated mucous is carried through the tubing 38 and exits opening 40 along with the compressed air. This mixture of compressed air and simulated mucous droplets spreads out in somewhat of a fan or fan-like pattern upon exiting the opening 40 thereby impacting the tissue sample material disposed between lower platen 18 and upper platen 20 through upper platen aperture 22. The combined force of the compressed air and simulated mucous droplets may or may not tear the tissue sample material disposed between lower platen 18 and upper platen 20 depending upon the strength of the tissue sample material disposed therebetween and disposed within the openings formed by upper platen aperture 22 and lower platen aperture 46. Exhaust valve 32 may be operated manually or electronically. However, it was found that electronic opening of exhaust valve 32 was preferred as the exhaust valve 32 was found to operate with greater celerity and in a more reproducible fashion than what a human operated manual valve could provide.

The seventh step 170 of method 100 provides for recordation and documentation of the break-through testing process and any results achieved by way of the testing method 100. It was found sufficient to simply record the test as a pass/fail result of the resulting break-through mode of the tissue product sample tested. Similar products (i.e., tissue samples) could be tested in a repetitive manner in order to demonstrate that the break-through strength of the tested tissue product sample is or is not sufficient to withstand a normal human sneeze. As would be understood by one of skill in the art, such test results could be photographed, videographed, charted as various forms of visual representation, or simply described as a comparison.

Figure 4:
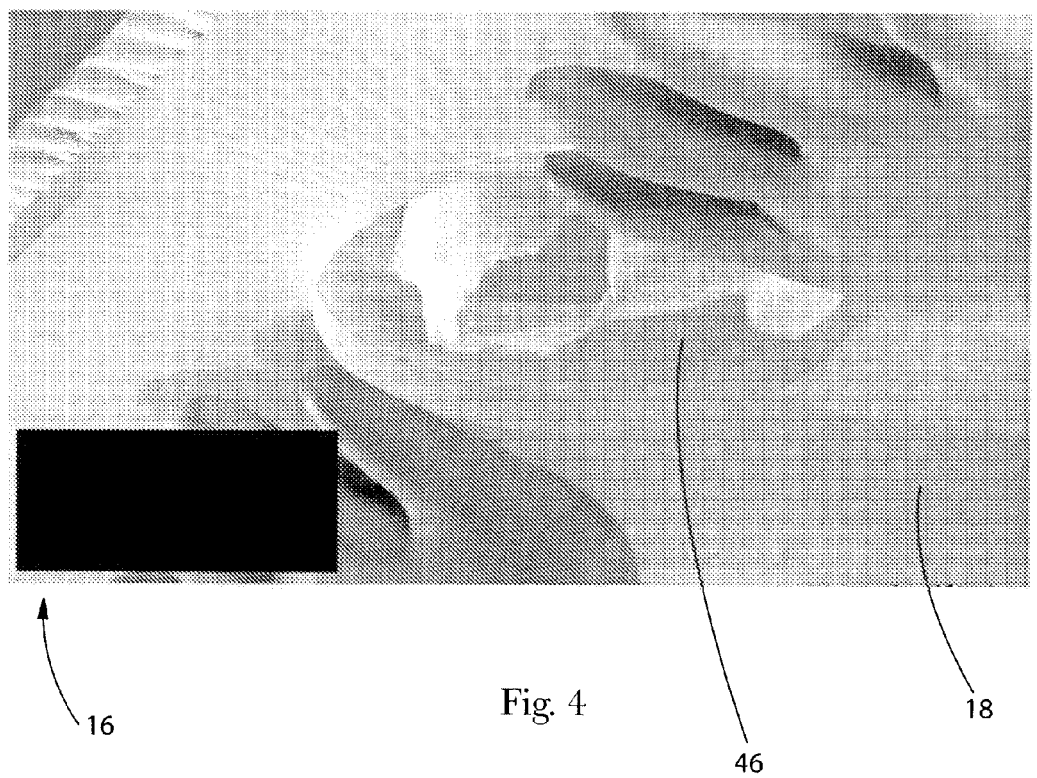
FIG. 4 is a photomicrograph of an exemplary facial tissue product exhibiting failure mode after testing by the break-through test apparatus of FIG. 1; and, FIG. 5 is a photomicrograph of an exemplary facial tissue product exhibiting success mode after testing by the break-through apparatus of FIG. 1.

An exemplary, but non-limiting, result recorded as a failure mode is shown in FIG. 4. FIG. 4 depicts a photomicrograph of an exemplary facial tissue product (Brand KC) subjected to testing by the overall method 100 and using break-through test apparatus 10 and of the present disclosure. As can be plainly seen, that portion of the sample disposed between lower platen 18 and upper platen 20 and disposed coextensive with upper platen aperture 22 and lower platen aperture 46 has a hole disposed therein indicating appreciable damage to the overall tissue product sample fiber structure. This photomicrograph was taken after testing with the break-through test apparatus 10 using method 100 described herein. This is what would be demonstratively and acceptably exhibited to a consumer as a failure mode.

Figure 5:
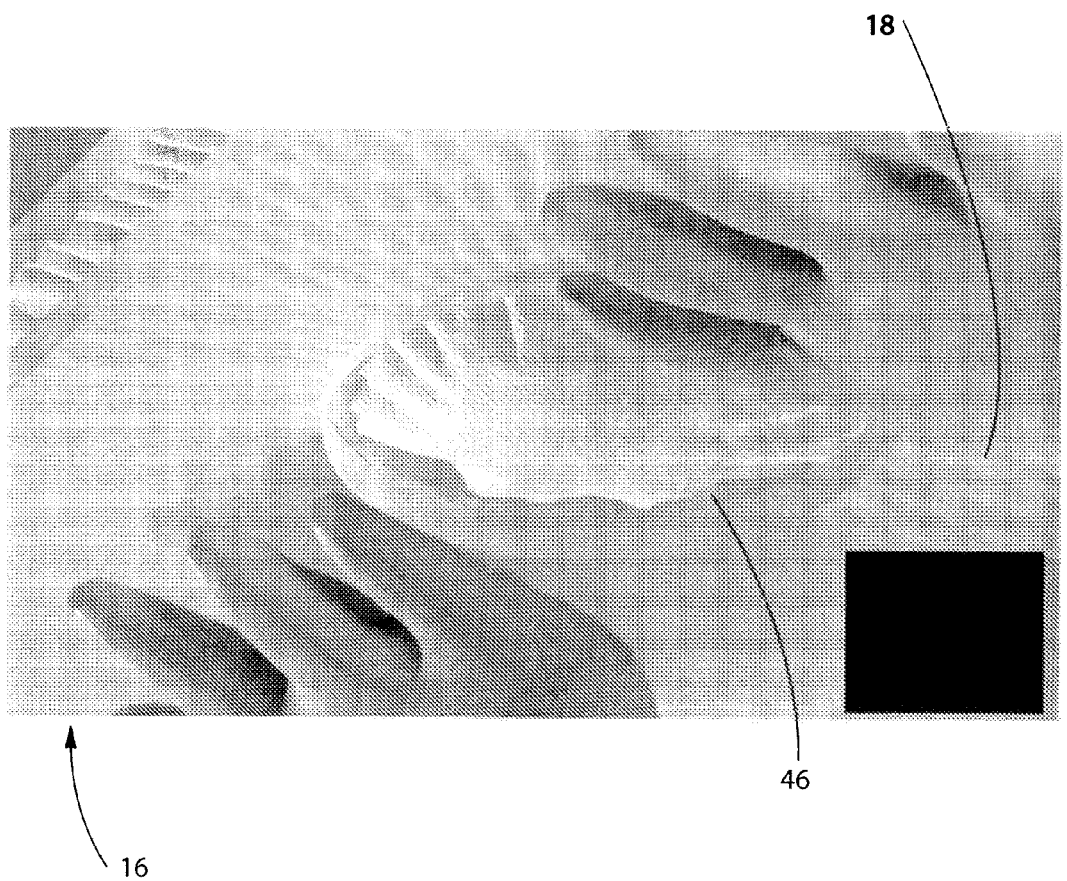

Alternatively, as shown in FIG. 5, an exemplary Puff's facial tissue (manufactured by The Procter & Gamble Company, Cincinnati, Ohio) exhibits a pass mode wherein the structure of the product disposed between lower platen 18 and upper platen 20 and coextensive with upper platen aperture 22 and lower platen aperture 46 does not exhibit any noticeable or appreciable damage to the overall tissue sample structure. This is what would be demonstratively and acceptably exhibited to a consumer as a pass mode.

One of skill in the art will also readily recognize that what would be demonstratively and acceptably exhibited to a consumer as a pass mode could also present an opportunity to quantitatively measure the amount of simulated mucous/compressed air that passes through the tissue sample yet does not cause appreciable damage to the overall tissue product sample fiber structure. In other words, the volume of simulated mucous/compressed air passing through the tissue sample yet not causing appreciable damage to the overall tissue product sample fiber structure can be measured. This circumstance would enable a person demonstrating the break-through strength of a tissue sample to also demonstrate the efficacy of the tissue sample in reducing the amount of product passing through the tissue sample. Thus, a sample could exhibit a pass mode as described above yet also be recognized for the amount of material (i.e., mucous) entrained by the tissue sample.

Such an evaluation could be accomplished by one of skill in the art with conventional sampling equipment. For example, the amount of mucous passing through a tissue sample can be collected in a container. This sample can then be volumetrically measured or quantitatively weighed to ascertain the amount of material collected. This process can be repeated for each sample tested. The resulting amounts collected can then be presented in a manner known to those of skill in the art to consumers to show yet another quality of various competitive products.

As required, break-through test apparatus 10 can be cleaned with distilled water, dried, and reset as indicated above for the next sample (tissue product or otherwise) to be tested. It is in this way that repetitive samples or sequential samples or even side-by-side samples of competitive consumer products can be tested to determine the overall qualitative break-through strength. For a side-by-side comparison, it would only be necessary to provide for at least two break-through test apparati (10) so that the various tissue product samples could be tested and observed in a side-by-side (i.e., comparative competitive) format. However, if only one break-through test apparatus 10 is provided for use with the overall method 100, it would necessarily be a truism that the tissue product samples would be tested one after the other in a sequential manner. In any regard, such observational characterization of the tissue product samples tested by the break-through test apparatus 10 of the instant disclosure can provide a clear indication to any consumer or any other person of the relative break-through strength of comparative products.

It would be readily recognized by one of skill in the art that the method of the present invention could be demonstrated to a consumer or any other audience, such a retailer or retail group, as a live, in-person demonstration. Alternatively, the method of the present invention could be recorded and stored by any means known in the art (i.e., conventional tape storage means (tape) or any digital storage means (compact disk) for later rebroadcast and/or re-transmission to a target audience such as a consumer or retail group. Such re-transmission could be conducted over conventional analog broadcast means such as television or other visual media, or over digital broadcast means including, but not limited to, digital television, the internet, video disks, and the like.

The dimensions and values disclosed herein are not to be understood as being strictly limited to the exact dimensions and values recited. Instead, unless otherwise specified, each such dimension and/or value is intended to mean both the recited dimension and/or value and a functionally equivalent range surrounding that dimension and/or value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method of demonstrating the comparative break-though strengths of at least two tissue products, the method comprising the steps of:
   a) providing a break-through test apparatus having a lower platen and an upper platen disposed in a face-to-face relationship;
   b) providing said at least two tissue products;
   c) observing a first condition of each of said at least two tissue products;
   d) disposing a first of said at least two tissue products between said lower platen and said upper platen in a face-to-face-to-face relationship;
   e) disposing at least a portion of said first tissue product between an aperture disposed within said lower platen and a coextensive aperture disposed within said upper platen;
   f) providing a simulated mucous composition;
   g) directing a first portion of said simulated mucous composition into contacting engagement with said first tissue product disposed within said coextensive apertures;
   h) after step g), observing a second condition of said first tissue product;
   i) disposing a second of said at least two tissue products between said lower platen and said upper platen in a face-to-face-to-face relationship and at least a portion of said second tissue product between said coextensive apertures;
   j) directing a second portion of said simulated mucous composition into contacting engagement with said second tissue product disposed within said coextensive apertures;
   k) after step j), observing a second condition of said second tissue product; and,
   l) comparing said second condition of said first tissue product and said second condition of said second tissue product.

2. The method of claim 1 further comprising the step of combining compressed gas with said simulated mucous composition.

3. The method of claim 2 wherein said steps of directing said simulated mucous composition toward said first and second tissue products each further comprise the step of expectorating said combined compressed gas and simulated mucous composition toward said first and second tissue products.

4. The method of claim 1 further comprising the step of formulating said simulated mucous composition from a mixture comprising carboxymethyl cellulose.

5. The method of claim 1 further comprising the step of, prior to step g), conditioning said simulated mucous composition.

6. The method of claim 1 further comprising the step of conditioning said first and second tissue product prior to testing.

7. The method of claim 1 wherein said steps of directing said simulated mucous composition toward said tissue products each further comprise the step of directing said simulated mucous composition toward each of said tissue products in a fan-like pattern.

8. The method of claim 1 wherein said steps of observing said second condition of said first and second tissue products each further comprise the step of observing whether any of said first and second tissue products exhibits a failure mode.

9. The method of claim 1 wherein said steps of observing said second condition of said first and second tissue products each further comprise the step of observing whether any of said first and second tissue products exhibits a pass mode.

10. The method of claim 1 further comprising the steps of recording said observations of said first condition of said first and second tissue products, recording said observations of said second condition of said first and second tissue products, and recording an observation of each of said first and second tissue products exhibiting a property selected from the group consisting of failure mode and pass mode.

11. The method of claim 1 further comprising the step of demonstrating said method of demonstrating the comparative break-though strengths of at least two tissue products to at least one consumer.

12. The method of claim 1 further comprising the step of recording said method of demonstrating the comparative break-though strengths of at least two tissue products.

13. The method of claim 12 further comprising the step of showing said recording of said method of demonstrating the comparative break-though strengths of at least two tissue products to at least one consumer.

14. A method of demonstrating the comparative break-though strengths of at least two tissue products, the method comprising the steps of:
   a) providing a first break-through test apparatus having a lower platen and an upper platen disposed in a face-to-face relationship;
   b) providing a second break-through test apparatus having a lower platen and an upper platen disposed in a face-to-face relationship;
   c) providing said at least two tissue products;
   d) observing a first condition of each of said at least two tissue products;
   e) disposing a first of said at least two tissue products between said lower platen and said upper platen of said first break-through test apparatus in a face-to-face-to-face relationship;
   f) disposing a portion of said first tissue product between an aperture disposed within said lower platen and a coextensive aperture disposed within said upper platen of said first break-through test apparatus;
   g) disposing a second of said at least two tissue products between said lower platen and said upper platen of said second break-through test apparatus in a face-to-face-to-face relationship;
   h) disposing a portion of said second tissue product between an aperture disposed within said lower platen and a coextensive aperture disposed within said upper platen of said second break-through test apparatus;
   i) providing a simulated mucous composition;
   j) directing a first portion said simulated mucous composition into contacting engagement with said first tissue product disposed within said coextensive apertures of said first break-through test apparatus and a second portion of said simulated mucous composition into contacting engagement with said second tissue product disposed within said coextensive apertures of said second break-through test apparatus;

k) observing a second condition of each of said first and second tissue products; and, l) comparing said second condition of said first tissue product and said second condition of said second tissue product.

15. The method of claim 14 wherein said step of observing said second condition of said first and second tissue products further comprises the step of observing whether any of said first and second tissue products exhibits a failure mode.

16. The method of claim 14 wherein said step of observing said second condition of said first and second tissue products further comprises the step of observing whether any of said first and second tissue products exhibits a pass mode.

17. The method of claim 14 further comprising the steps of recording said observations of said first condition of said first and second tissue products, recording said observations of said second condition of said first and second tissue products, and recording an observation of each of said first and second tissue products exhibiting a property selected from the group consisting of failure mode and pass mode.

18. The method of claim 14 further comprising the step of demonstrating said method of demonstrating the comparative break-though strengths of at least two tissue products to at least one consumer.

19. The method of claim 14 further comprising the step of recording a demonstration of said method of demonstrating the comparative break-though strengths of at least two tissue products.

20. The method of claim 19 further comprising the step of showing said recording of said method of demonstrating the comparative break-though strengths of at least two tissue products to at least one consumer.

* * * * *